US00PP19032P2

(12) United States Plant Patent
Radler

(10) Patent No.: US PP19,032 P2
(45) Date of Patent: Jul. 15, 2008

(54) ***SHRUB ROSE* PLANT NAMED 'RADSWEET'**

(50) Latin Name: *Rosa hybrida*
Varietal Denomination: cv. Radsweet

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 33 days.

(21) Appl. No.: 11/650,979

(22) Filed: Jan. 9, 2007

(51) Int. Cl.
*A01H 5/00* (2006.01)

(52) U.S. Cl. ..... Plt./107
(58) Field of Classification Search ..... Plt./107
See application file for complete search history.

(56) References Cited

U.S. PATENT DOCUMENTS

| | | | | | |
|---|---|---|---|---|---|
| PP9,261 | P | * | 8/1995 | Olesen et al. | Plt./107 |
| PP11,836 | P2 | * | 4/2001 | Radler | Plt./108 |
| PP16,544 | P2 | * | 5/2006 | Olesen | Plt./107 |
| PP18,562 | P2 | * | 3/2008 | Radler | Plt./104 |

* cited by examiner

*Primary Examiner*—Wendy C. Haas
(74) *Attorney, Agent, or Firm*—Buchanan Ingersoll & Rooney PC

(57) ABSTRACT

A new and distinct variety of shrub rose plant is provided which forms in abundance on a substantially continuous basis attractive single blossoms that are light pink in coloration. The vegetation is vigorous and strong and the growth habit is compact, spreading, and mounding. Attractive ornamental leathery medium-green foliage having a matte finish is formed. Excellent resistance with respect to blackspot and rose midge is displayed. The new variety is particularly well suited for growing as distinctive ornamentation in the landscape.

2 Drawing Sheets

Botanical/commercial classification: *Rosa hybrida*/Shrub Rose Plant.
Varietal denomination: cv. Radsweet.

SUMMARY OF THE INVENTION

The new variety of *Rosa hybrida* shrub rose plant of the present invention was created at Greenfield, Wis., U.S.A., by artificial pollination wherein two parents were crossed which previously had been studied in the hope that they would contribute the desired characteristics. The female parent (i.e., the seed parent) was the 'Radtee' variety (non-patented in the United States). The male parent (i.e., the pollen parent) of the new variety was the 'Radral' variety (non-patented in the United States). The parentage of the new variety can be summarized as follows:

'Radtee'×'Radral'.

The seeds resulting from the above pollination were sown and small plants were obtained which were physically and biologically different from each other. Selective study resulted in the identification of a single plant of the new variety.

I was attracted to the new variety primarily because of its distinctive light pink blossom coloration and attractive foliage. When mature the blossoms were found to assume an even lighter pink apple-blossom coloration approaching white particularly when exposed to increasing temperatures.

It was found that the new shrub rose plant of the present invention possesses the following combination of characteristics:

(a) abundantly and substantially continuously forms attractive single blossoms that are light pink in coloration, (b) exhibits a compact, spreading, and mounding growth habit, (c) forms vigorous vegetation, (d) forms attractive leathery medium-green foliage with a matte finish, and (e) exhibits excellent resistance to blackspot and rose midge.

A new rose variety is provided having attractive light-pink blossoms combined with a propensity for everblooming and disease resistance. The blooming cycle corresponds closely to that of the 'Radrazz' variety (U.S. Plant Pat. No. 11,836). The foliage displays a sweetbriar fragrance.

The new variety well meets the needs of the horticultural industry. It can be grown to advantage as ornamentation in parks, gardens, public areas, and in residential settings. The new variety is particularly well suited for providing attractive ornamentation in the landscape. The light-pink blossoms contrast nicely with the medium-green foliage.

The new variety of the present invention also can be readily distinguished from its ancestors through an inspection of the blossoms. More specifically, the 'Radtee' variety forms smaller flowers with more petals that tend to lack the ability to self-clean. Also, the new variety displays more of a sweetbriar foliage fragrance than that of the 'Radtee' variety. The 'Radral' variety forms even lighter pink blossoms, a taller growth habit, glossy foliage, and displays less disease resistance that the new variety. Also, the foliage of 'Radral' variety lacks a sweetbriar foliage fragrance unlike the foliage of the new variety.

The characteristics of the new variety have been found at Waso, Calif., U.S.A., and near West Grove, Pa., U.S.A., to be homogeneous and stable and to be strictly transmissible by asexual propagation such as budding, grafting, and the rooting of cuttings from one generation to another. The new variety reproduces true to type by such asexual propagation.

The new variety has been named 'Radsweet'.

BRIEF DESCRIPTION OF THE PHOTOGRAPHS

The accompanying photographs show, as nearly true as it is reasonably possible to make the same in color illustrations of this character, typical specimens of the new variety. The illustrated rose plants of the new variety were approximately two years of age and were observed during July while growing outdoors in the ground on their own roots near West Grove, Pa., U.S.A.

DETAILED DESCRIPTION

Figure 1:
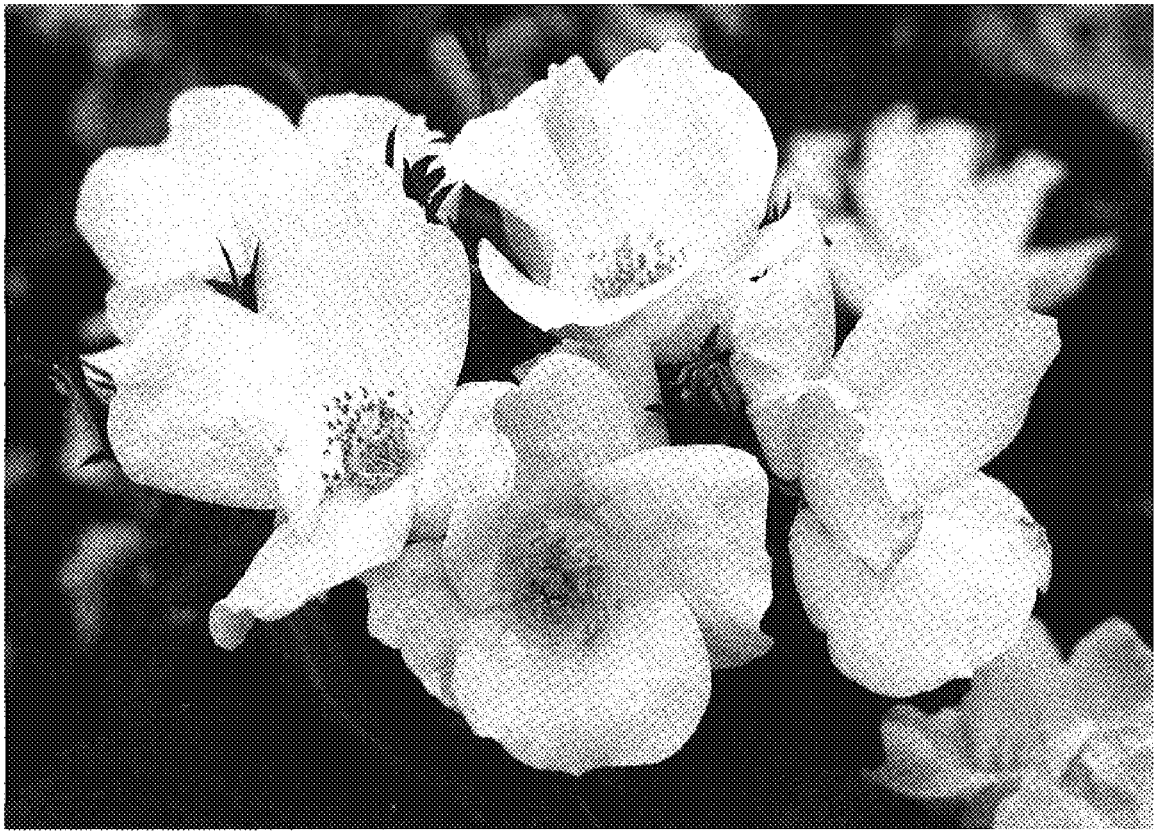
FIG. 1 shows typical blossoms in various stages of maturity and a bud of the new variety.
Figure 2:
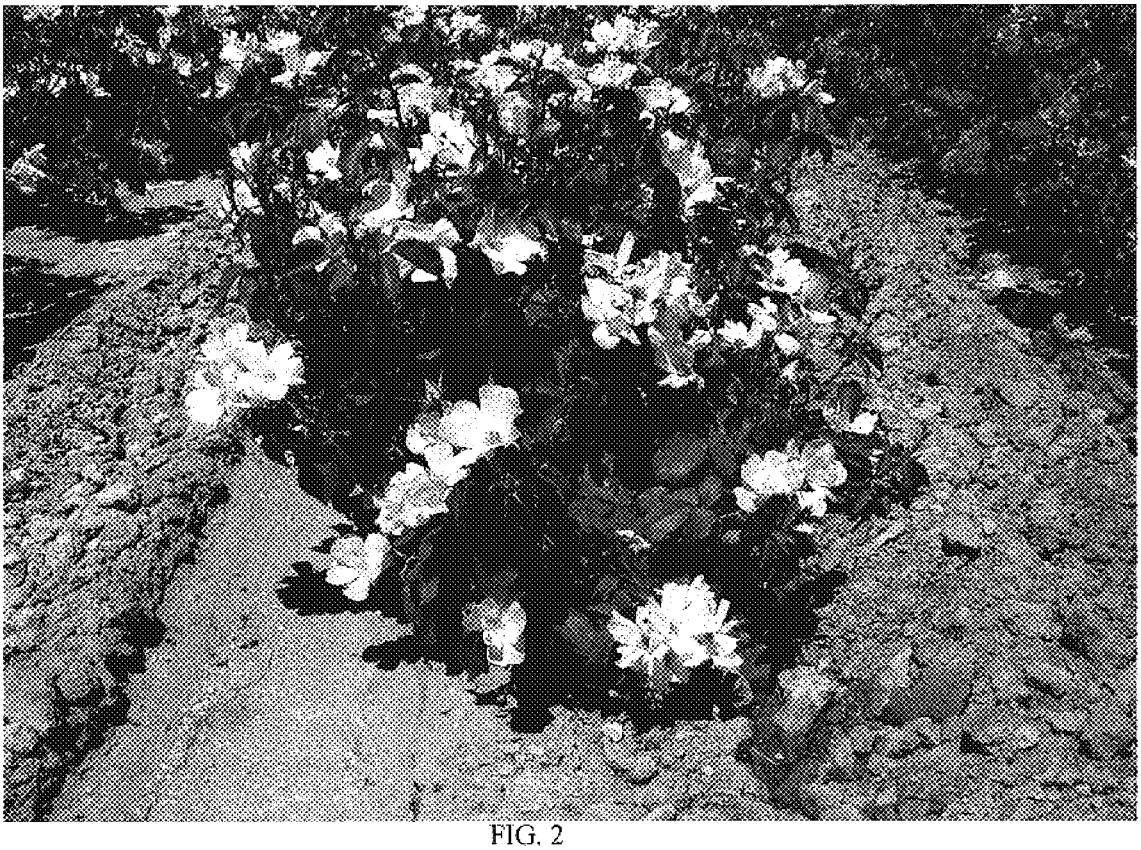
FIG. 2 shows a flowering plant wherein the attractive compact growth habit and foliage are illustrated.

The chart used in the identification of colors is that of The Royal Horticultural Society (R.H.S. Colour Chart), London, England. The description is based on the observation of two-year-old specimens of the new variety during July while growing outdoors in the ground on their own roots near West Grove, Pa., U.S.A.

Class: Landscape Shrub.

Plant:

*Height.*—Approximately 75 to 100 cm on average at the end of the growing season.

*Width.*—Approximately 75 to 100 cm on average at the end of one growing season.

*Habit.*—Compact, spreading, and mounding.

Branches:

*Color.*—Young stems: slightly glaucous, and commonly near Yellow-Green Group 144A, 144B, and 144C.

*Thorns.*—Size: approximately 1 to 1.6 cm in length on average, and approximately 0.8 to 1.2 cm in width at the base parallel to the stem. The larger thorns typically are present near the base of the more vigorously growing stems that become flowering shoots. Shape: the upper edge tends to be more or less straight and to point downwards at an angle of approximately 25 to 40° below the horizontal, the lower edge commonly is convex when viewed from above, and the base configuration is slightly ovate with some narrowing forwards the base. Quantity: at the lower portion of a flowering stem approximately 8 to 12 thorns on average are present over a length of 15 cm, and at the upper portion of a flowering stem very few thorns are present of any size. Color: variable and commonly near Green Group 138B, 138C, and 139C with some purplish color in the greatest concentration near Greyed-Purple Group 185A at the base which tends to appears as a wash.

Leaves:

*Size.*—Approximately 8 to 16 cm in length, and approximately 8 to 15 cm in width. The overall size has been found to vary greatly. Leaves measuring outside the specified ranges sometimes appear with their size being influenced by the time within the growing season, the plant vigor being displayed, location on the stem, and environmental and cultural conditions being experienced. The leaves with fewer leaflets tend to display the smaller overall leaf size.

*Stipules.*—Configuration: revolute with two prominent reflexed horns and an elliptical body. Length: approximately 1.3 to 2.9 cm (average approximately 1.9 cm) from the tip of the base to the tip of the longest horn. Width: approximately 0.5 to 1.2 cm (average approximately 0.8 cm) across the tips of the horns, and approximately 0.3 to 0.8 cm (average approximately 0.6 cm) at the widest portion of the body. Color (young wings): near Greyed-Purple Group 185A on the upper surface and near Greyed-Purple 186A on the under surface. Color (mature wings): near Green Group 137A on the upper surface and near Green Group 137B on the under surface. Margin: serrulate to dentriculate with each tooth commonly being terminated with a reddish somewhat stiff hardened tip. Texture: wings of young stipules tend to be glaucous, and wings of mature stipules tend to bear short reddish hairs at the margin and near the petiole having lengths approximately 0.1 to 0.2 mm that are near Greyed-Purple Group 187A and 187B in coloration.

*Petioles.*—Length: typically approximately 1.5 to 2.5 cm, and most commonly approximately 1.7 to 2.0 cm. Diameter: typically approximately 1.3 to 2.0 mm, and most commonly approximately 1.3 to 1.5 mm. Color (upper surface): near Green Group 137B and 138A. Color (under surface): Yellow-Green Group 144A and 146C. Texture (upper surface): bear stiff glandular hairs having lengths of approximately 0.1 to 0.5 mm. Texture (under surface): also bear such stiff glandular hairs but commonly at a lesser frequency, and bear a few scattered minute reddish prickles that are near Greyed-Purple Group 186A in coloration and typically are approximately 0.8 to 1.2 mm in length and most commonly approximately 0.8 to 1.2 mm in length. Also, each petiole commonly bears 1 or 2 larger prickles; however, up to 5 prickles sometimes have been observed.

*Petiolules.*—The upper and lower surfaces commonly are near Red-Purple Group 187A in coloration.

*Rachis.*—Length: typically approximately 1.0 to 2.5 cm, and most commonly approximately 1.8 to 2.0 cm. Diameter: typically approximately 1.0 to 2.1 mm, and most commonly approximately 1.3 to 1.6 mm. Color (upper surface): when mature near Yellow-Green Groups 146B, and commonly with some coloration of near Green Group 137C and Yellow-Green Group 146C. Color (under surface): when mature near Green Group 143C and Yellow-Green Group 146C. Texture: similar to that of the petioles.

*Leaflets.*—Number: 3, 5, and 7 (with 3 and 5 being more common). Arrangement: alternate and odd-pinnately compound. Shape: narrowly elliptical to elliptical to slightly ovate. Size: terminal leaflets typically are 5.5 to 8.5 cm (commonly 6.5 to 7.5 cm) in length, and typically are 2.5 to 4.5 cm (commonly 3 to 4 cm) in width. Base: broadly rounded to broadly cuneate to inequilaterus or strongly obtuse. Apex: broadly acuminate to abruptly acuminate. Margins: serrate to serrulate that commonly is slightly to occasionally strongly revolute. Texture: leathery with a matte finish. Overall appearance: very dense, and medium green in coloration. Color (young foliage): both surfaces are near Greyed- Purple Group 187A and 187B over a green base coloration, and the venation may include coloration of Red-Purple Group 59A, and the margins when undergoing development may include coloration of Red-Purple Group 59A and Greyed-Purple Group 185A. Color (adult foliage): Upper surface: near Green Group 137A on the lighter foliage and near Green Group 139A on the darker foliage. Under surface: near Greyed-Green Group 191A commonly with veins near Yellow-Green Group 146C.

Inflorescence:

*Number of flowers.*—Commonly approximately 2 to 3 blooms on average in a cluster, occasionally solitary, sometimes up to 5 or more blooms in a cluster, and as many as 40 blooms have been observed on a vigorous stem during some observations.

*Sepals.*—Length: commonly approximately 18 to 27 mm, and approximately 22 mm on average. Width: commonly approximately 4 to 7 mm at the widest point, and approximately 5.5 mm on average. Extensions: commonly present and feathery foliaceous, the frequency often ranges from 0 to 6 or more plus an expanded feathery tip, typically the shortest sepal has no foliaceous extensions, typically the next shortest sepal has no foliaceous extensions or occasionally 1 and rarely 2 foliaceous extensions, typically the third shortest extension has 2 or 3 and occasionally 4 foliaceous extensions, and typically the 2 longest sepals have 4 or 5 and occasionally 6 foliaceous extensions plus the longest and most feathered tips. Apex: commonly narrowly acuminate to acuminate when lacking a foliaceous extension. Base: commonly fused to the receptacle and to adjoining sepals, and hence there is no distinct base configuration. Overall shape: substantially lanceolate. Texture: the interior surface commonly is moderately densely covered with a silvery-white lanate hairs giving an effective color of near White Group 155C with a light greenish hue to the hairs which overlay green base tissue, at the margins small reddish-tipped glandular hairs typically are present which commonly are approximately 0.1 to 0.5 mm in length and tend to be more common on sepals which bear foliaceous extensions, and such glandular hairs are also commonly sparsely scattered across the outer surfaces of the sepals and are common on sepals which bear foliaceous extensions. Color: commonly near Green Group 137C, 143A, and 143B, and Yellow-Green Group 144A and 144B. On the outer surface the foliaceous extensions commonly appear to be somewhat transparent and bear coloration of Greyed-Purple Group 187B with some green showing through. Number: five.

*Buds.*—Shape: generally ovoid. Length: approximately 1.3 to 1.5 cm on average. Diameter: approximately 0.8 to 1.2 cm. Size: small. Color (at bud crack): commonly Red-Purple Group 63C. Color (during further opening): rapidly lightens and changes to near and through Red-Purple Group 62A, 62B, 62C, and Red Group 36D.

*Flower.*—Form: single. Shape: informal. Diameter: commonly approximately 5 to 7 cm on average during mid-summer, and is somewhat variable depending upon the time of the year and the vigor the plant. Color (when blooming): Upper surface: the distal portions commonly are near Red-Purple Group 62A, 62B, and 62C, to near White Group 155D, and with the inner petals sometimes displaying darker areas of Red-Purple Group 68A and 68B which in some instances may appear as thin lines. The veins tend to impart no different coloration and may be substantially colorless. Under surface: when fully open the coloration tends to be substantially the same as that of the upper surface. Red-Purple Group 73C may predominate towards the tip with occasional darker areas of Red-Purple Group 73A and 73B. This coloration lightens with maturity to Red-Purple Group 62C and 62D to near White Group 155D and near Yellow Group 4C and 4D at the base. Occasional spots and darker areas of Red-Purple Group 68A and 68B are present. Lastingness: the coloration is somewhat sensitive to heat and light which tend to lighten the initial pink coloration. Flowers that develop during the hotter months display coloration that is lighter pink and fades to near apple-blossom white. During the cooler months the flowers are medium-light pink in coloration. Fragrance: light. Petal form: narrowly to broadly obovate. Petal number: approximately 6 to 11, and commonly 7 to 9 on average. Petal base: narrowly cuneate to cuneate to narrowly rounded to rounded. Petal apex: broadly obtuse to rounded to truncate and rarely broadly acute, softly apiculate to occasionally slightly emarginated, occasionally slightly praemorsus, and tends to become revolute as the flower matures. Petal margin: mostly entire, and occasionally becoming slightly undulate towards the apex. Petaloid number: commonly 0 to approximately 5, and most commonly approximately 2 per flower on average. Petaloid shape: highly variable, and most commonly falcate. Petaloid length: approximately 10 to 29 mm across the arc. Petaloid width: approximately 3 to 19 mm at the widest point. Petaloid texture: typically opaque, glabrous, and soft. Petaloid color (both sides): near Red-Purple Groups 62A, 62B, 62C and 62D with Red-Purple Group 62B and 62C being prominent, Red Group 49D to White Group 155C and 155D towards the base, and Yellow Group 4C at the very base. Also, some petaloids display areas of Red-Purple Group 68A and 68B that appear as scattered darker areas that typically are present on the inner surface and towards the edges. Lasting quality: blossoms commonly last approximately 1½ to 2 weeks on the plant depending upon environmental conditions, and sometimes up to 10 days when cut and placed in a vase. Petal drop: very good, the petals drop cleanly and freely. However, under prolonged rainy growing conditions the petals may persist somewhat. Stamen number: approximately 100 on average. Anther size: immediately prior to and during anthesis approximately 1.2 to 2 mm in length. Anther color: Greyed-Yellow Group 160A and 160B when the flowers first open, and with changing maturity Greyed-Orange Group 163C. Filament length: variable and commonly approximately 2 to 10 mm. Filament color: Yellow-Orange Group 20A near the base, thereafter towards the anther Yellow-Orange Group 20B, and Yellow Group 13B and 13C immediately adjacent the anther. Pollen: it appears that viable pollen is formed in a sparse quantity, no active pollen discharge is observed in the flowers, and when the anther is crushed some yellow-orange pollen has been observed. Pistils: commonly approximately 32 to 40, and approximately 37 on average. Stigma size:

commonly approximately 0.5 to 0.9 mm in diameter, and approximately 0.7 mm on average. Stigma color: Greyed-Yellow Group 162A. Style length: commonly approximately 8 to 11 mm, approximately 9 mm on average, and commonly with kinks. Style color: near Greyed-Purple 185B and 185C through Red-Purple Group 60B and 60C, and approaching Greyed-Purple Group 185A with the lightest coloration being present at the base. Receptacle length: commonly approximately 7.5 to 9.5 mm, and approximately 8.5 mm on average. Receptacle width: commonly approximately 6.2 to 7.5 mm, and approximately 6.5 mm on average. Receptacle texture: glaucous with a waxy coating, commonly smooth over approximately 75 percent of the surface, the lower 25 percent of the surface commonly bears scattered minute stiff reddish glandular hairs and occasional prickles having length of approximately 0.1 to 1 mm and a coloration of near Greyed-Purple Group 187B that are more common on the lower approximately 10 to 15 percent of the surface. Receptacle color: near Green Group 143A and 143B.

Development:

*Vegetation.*—Vigorous and strong.

*Blossoming.*—Abundant and substantially continuous during the growing season.

*Resistance to diseases.*—Excellent with respect to blackspot.

*Resistance to pests.*—Excellent with respect to rose midge.

*Formation of hips/seeds.*—None observed to date when grown in a greenhouse, and when grown outdoors a small quantity of fruit has set. It is not known whether such fruit is viable.

The 'Radsweet' variety has not been observed under all possible environmental conditions to date. Accordingly, it is possible that the phenotypic expression may vary somewhat with changes in light intensity and duration, cultural practices, and other environmental conditions.

I claim:

1. A new and distinct shrub rose plant characterized by the following combination of characteristics:

(a) abundantly and substantially continuously forms attractive single blossoms that are light pink in coloration, (b) exhibits compact, spreading, and mounding growth habit, (c) forms vigorous vegetation, (d) forms attractive leathery medium-green foliage with a matte finish, and (e) exhibits excellent resistance to blackspot and rose midge;

substantially as herein shown and described.

* * * * *